(12) United States Patent
Ideta et al.

(10) Patent No.: US 8,043,817 B2
(45) Date of Patent: Oct. 25, 2011

(54) METHOD OF DETERMINING EFFICIENCY OF OVUM COLLECTION IN BOVINE

(75) Inventors: Atsushi Ideta, Hokkaido (JP); Yoshito Aoyagi, Hokkaido (JP); Mayumi Sugimoto, Fukushima (JP); Yoshikazu Sugimoto, Fukushima (JP)

(73) Assignees: Zen-Noh, Tokyo (JP); Japan Livestock Technology Association, Tokyo (JP); National Livestock Breeding Center, Incorporated Administrative Agency, Fukushima (JP)

( * ) Notice: Subject to any disclaimer, the term of this patent is extended or adjusted under 35 U.S.C. 154(b) by 238 days.

(21) Appl. No.: 12/482,988

(22) Filed: Jun. 11, 2009

(65) Prior Publication Data

US 2009/0311705 A1    Dec. 17, 2009

(30) Foreign Application Priority Data

Jun. 12, 2008 (JP) ................. 2008-153767

(51) Int. Cl.
*C12Q 1/68* (2006.01)
*C12P 19/34* (2006.01)

(52) U.S. Cl. .............. 435/6.17; 435/6.11; 435/6.12
(58) Field of Classification Search ................ None
See application file for complete search history.

(56) References Cited

OTHER PUBLICATIONS

See NCBI dbSNP submitted SNP (ss) details: ss65441349 obtained from http://www.ncbi.nlm.nih.gov/SNP/snp_ss.cgi?subsnp_id=65441349[Jul. 11, 2011 3:11:19 PM]; two pages.*

* cited by examiner

*Primary Examiner* — Juliet Switzer
(74) *Attorney, Agent, or Firm* — Birch, Stewart, Kolasch & Birch, LLP

(57) ABSTRACT

The novel means by which an efficiency of ovum collection can be easily determined in bovine at gene level is disclosed. The present inventors performed the genomic linkage analysis using bovine populations with high and low efficiency of ovum collection and to identify GRIA1 gene, which encodes an ion channel protein, as a factor deeply related to an efficiency of ovum collection. Bovines having a mutation (e.g. the amino acid substitution of aa306) in GRIA1 produce significantly fewer ova on superovulatory treatment than those not having the mutation. Therefore, the efficiency of ovum collection can be determined based on the existence of a mutation in GRIA1 gene.

14 Claims, 1 Drawing Sheet

```
         10         20         30         40         50         60
AGCCTCCCTA CCAGCTCTCT CTCTGACACC CAACTGTCTC TGTTCCTCCC ACCAGTACAC
─────────────────────▶

70         80         90        100        110        120
CTCTGCGCTC ACCTACGATG GGGTGAAGGT GATGGCTGAG GCTTTCCAGA GCCTGCGGAG 130        140        150        160        170        180
GCAGAGAATT GATATCTCCC GCCGGGGGAA TGCTGGGGAC TGCCTGGCTA ACCCAGCTGT 190        200        210        220        230        240
GCCCTGGGGC CAGGGCATCG ACATCCAGAG AGCTCTGCAG CAG GTGAGGC TGGCAACAAC G
                                                ◀─────────────────
```

METHOD OF DETERMINING EFFICIENCY OF OVUM COLLECTION IN BOVINE

This application claims the priority of Japanese Patent Application No. 2008-153767 filed Jun. 12, 2008, the entire contents of which are hereby incorporated by reference into the present application.

FIELD OF THE INVENTION

The present invention relates to a method of determining efficiency of ovum collection in bovine, a kit used for carrying out the same, and a reagent for determining efficiency of ovum collection in bovine.

BACKGROUND OF THE INVENTION

It is important to obtain many descendants of the individual having an excellent property in proceeding a breeding of bovine animals. In conventional breeding methods, bovines are typically subjected to a superovulatory treatment to obtain a lot of ova. However, due to the individual differences, the average number of the ova collected by single superovulatory treatment widely varies between 0 to 50.

How many ova a bovine can produce upon a superovulatory treatment is of hereditary nature. If any genetic markers, for example, polymorphism correlated with the above-mentioned individual difference can be identified, the bovines with a high efficiency of ovum collection can be rapidly identified, which accelerates breeding of bovines. However, since no genomic information concerning efficiency of ovum collection has been clarified, breeders must control the efficiency of ovum collection mainly based on how to treat and care the bovines.

REFERENCES

1. Hunter M G, Robinson R S, Mann G E, Webb R. Endocrine and paracrine control of follicular development and ovulation rate in farm species. Anim. Reprod. Sci. 2004; 82-83: 461-477.
2. Baracaldo M I, Martinez M F, Adams G P, Mapletoft R J. Superovulatory response following transvaginal follicle ablation in cattle. Theriogenology 2000; 53: 1239-1250.
3. D'Occhio M J, Jillella D, Lindsey B R. Factors that influence follicle recruitment, growth and ovulation during ovarian superstimulation in heifers: opportunities to increase ovulation rate and embryo recovery by delaying the exposure of follicles to LH. Theriogenology 1999; 51: 9-35.
4. Yamazaki M, Ohno-Shosaku T, Fukuya M, Kano M, Watanabe M, Sakimura K. A novel action of stargazing as a an enhancer of AMPA receptor activity. Neurosci. Res. 2004; 50: 369-374.
5. Brann D W, Mahesh V B. Excitatory amino acids: evidence for a role in the control of reproduction and anterior pituitary hormone secretion. Endocr. Rev. 1997; 18: 678-700.
6. Dziedzic B, Prevot V, Lomniczi A, Jung H, Cornea A, Ojeda S R. Neuron-to-gila signaling mediated by excitatory amino acid receptors regulates erbB receptor function in astroglial cells of the neuroendocrine brain. J. Neurosci. 2003; 23: 915-926.

SUMMARY OF THE INVENTION

Accordingly, an object of the present invention is to provide means by which an efficiency of ovum collection can be easily determined in bovine at gene level.

The present inventors intensively studied to succeed in identifying GRIA1 gene, which encodes ion channel, as a factor deeply related to an efficiency of ovum collection. The inventors also found that a single base substitution in the coding region of GRIA1 gene leads to the amino acid substitution of serine at aa306 to asparagine in GRIA1 protein, and that the amino acid substitution results in the reduced channel activity of GRIA1. The inventors further found that both the immature ovarian follicles observed in the ovary before superovulation and the ova collected after superovulation are reduced in bovines which have the substitution mutation, compared with ones which do not have, thereby completing the present invention.

That is, the present invention provides a method of determining efficiency of ovum collection in bovine, said method comprising examining whether the bovine has at least one mutation in GRIA1 gene or not, said mutation resulting in an abnormal GRIA1 protein. The present invention also provides a kit for determining efficiency of ovum collection in bovine by the method according to claim 7, said kit comprising a primer set, each primer of said set specifically hybridizing with a partial region of the base sequence shown in SEQ ID NO:1 or NO:5. The present invention further provides a reagent for determining efficiency of ovum collection in bovine, said reagent comprising a primer hybridizing specifically with a partial region of the base sequence shown in SEQ ID NO:1 or NO:5.

By the present invention, means by which the efficiency of ovum collection can be determined in a bovine by using as an index a gene mutation, referring to its base sequence, was firstly provided. Although the efficiency of ovum collection is a quantitative character to which a plurality of genes are related, the efficiency can be easily determined by using as an index a mutation in just one gene in accordance with the present invention. Therefore, the present invention can improve the efficiency and the speed of breeding of bovines.

DETAILED DESCRIPTION OF THE INVENTION

Figures 1, 2:
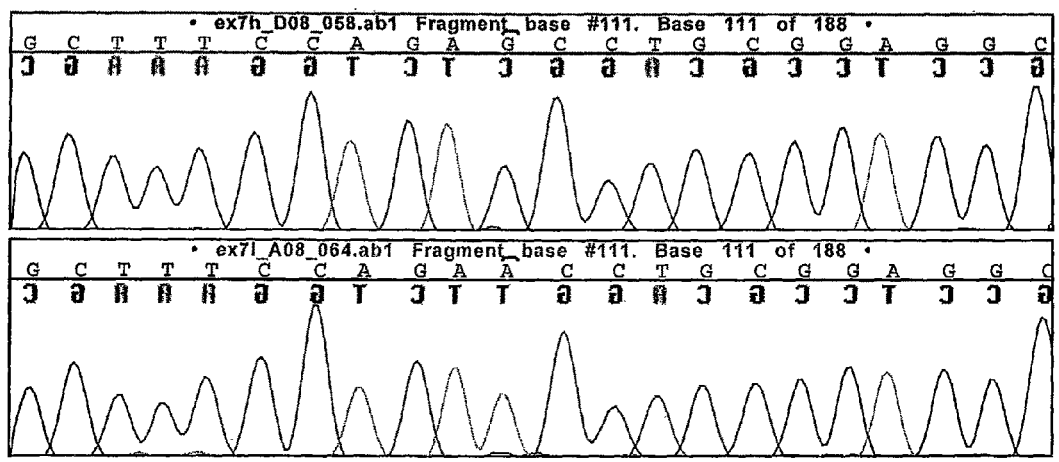
FIG. 1 shows the mutation site in GRIA1 gene genomic sequence identified in Examples. Boxes indicate the region with which the primer for detecting the mutation hybridizes, and arrows indicate the direction of each primer (5' to 3').
FIG. 2 shows a part of the sequencing data of the PCR product amplified by the primer set prepared in Examples, which primer set can amplify the region containing the mutation site identified in Examples. Upper row shows the sequencing data of the PCR product derived from normal genomic GRIA1 gene, and lower row shows that of the PCR product derived from abnormal genomic GRIA1 gene. As shown therein, 11th base counted from the left side is G in the normal type (upper), while A in the abnormal type (lower).

It should be understood that this invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "an abnormal protein" includes a plurality of such abnormal proteins.

In a method of the present invention, bovine GRIA1 gene is used as an index. GRIA1 is a gene which encodes an ion channel protein. Although the gene per se is known, the fact that GRIA1 gene is related to the efficiency of ovum collection is what the present inventors firstly discovered using linkage analysis and positional cloning (see, Examples below).

The term "abnormal GRIA1" and "abnormal type" as used herein refer to a GRIA1 variant which naturally occurs and whose activity as GRIA1 protein is decreased or diminished. Examples of such abnormal GRIA1s include the variant having an amino acid substitution of the 306th amino acid (hereinafter referred to as "aa306"), serine, to asparagine as shown in Example described below. Examples thereof also include other naturally-occurring variants such as truncated GRIA1s, GRIA1 variants having substitution and/or deletion of one or more amino acids which are important for GRIA1 activity, GRIA1 variants having one or more amino acid insertions in the region which is important for GRIA1 activity and the like. It is understood that the expression "aa306 of GRIA1" herein is used to refer to the position of the amino acid in any GRIA1 based on the amino acid sequence of wild type GRIA1 shown in SEQ ID NO:2. It is apparent for those skilled in the art that which amino acid in various GRIA1 variants whose sequences are different from wild type GRIA1 corresponds to aa306 in SEQ ID NO:2. Concretely, which amino acid in a certain GRIA1 variant corresponds to aa306 in wild type GRIA1 can be confirmed by aligning the amino acid sequences of wild type GRIA1 and the GRIA1 variant by using well-known program such as BLAST, CLUSTAL W or the like, while appropriately inserting one or more gaps thereto, so that the amino acid at the same position as aa306 in wild type GRIA1 is identified as the corresponding amino acid in the variant.

On the other hand, the term "normal GRIA1" as used herein includes not only wild type GRIA1 having the amino acid sequence shown in SEQ ID NO:2, but also any naturally-occurring variants which have the same bioactivity as the wild type GRIA1. It should be understood that when proteins are simply referred to as "GRIA1", the term "GRIA1" includes both normal and abnormal GRIA1, unless otherwise apparent from the context.

In the present specification and in the claims, "Xnt" (X represents a certain number) refers to the Xth base from the 5'-end of the mentioned base sequence, i.e., the Xth base counted from 1st base of the base sequence described in SEQUENCE LISTING. Similarly, "aaX" refers to the Xth amino acid from the N-terminal of the mentioned amino acid sequence, i.e., the Xth amino acid counted from 1st amino acid of the amino acid sequence described in SEQUENCE LISTING. For example, the phrase "1nt-916nt region of the base sequence shown in SEQ ID NO:1" means the region consisting of 1st to 916th base of the base sequence shown in SEQ ID NO:1.

As GRIA1 is a ion channel protein, the activity of any variant GRIA1 (normal or abnormal GRIA1) as GRIA1 can be easily assessed by, for example, introducing GRIA1 gene into an appropriate cells such as frog oocytes or the like by a conventional method, and then measuring the membrane current after the conventional glutamic acid stimulation, as described in Examples below. Therefore, those skilled in the art can easily confirm whether a GRIA1 protein encoded by GRIA1 gene having (a) certain mutation(s) is abnormal or not.

As shown in Examples below, bovines having GRIA1 gene with (a) mutation(s) which result(s) in an abnormal GRIA1 have lower capacity to produce ova upon superovulatory treatment, compared with those having normal GRIA1 gene. In those having normal GRIA1 gene, the possibility to obtain 10 or more ova on an average by single superovulatory treatment is high. Therefore, by examining whether the GRIA1 gene in a bovine has such (a) mutation(s) resulting in an abnormal GRIA1 or not, it can be determined whether the efficiency of ovum collection of the bovine (capacity to produce ova when the bovine receives a superovulatory treatment) is good or not. The superovulatory treatment per se is a conventional well-known method in the field of breeding livestock.

Examples of the mutation resulting in the expression of an abnormal GRIA1 include missense or nonsense mutation. Specific examples of the mutation which can be used as an index in the present invention include the missense mutation which is the amino acid substitution of aa306 serine to asparagine, as identified in Examples below. Such the missense mutation at aa306 may be caused by, for example, the single base substitution of 917nt guanine in GRIA1 gene to adenine, as shown in Examples below. The position of the single base substitution as mentioned herein is referred to based on cDNA sequence of the wild type GRIA1 gene, i.e. the base sequence shown in SEQ ID NO:1. It is apparent for those skilled in the art that which base in various GRIA1 gene variants whose sequences are different from wild type GRIA1 gene corresponds to 917nt in SEQ ID NO:1. Concretely, which base in a certain GRIA1 gene variant corresponds to 917nt in wild type GRIA1 cDNA can be confirmed by aligning the cDNA sequences of wild type GRIA1 gene and the variant GRIA1 gene by using well-known program such as BLAST, CLUSTAL W or the like, while appropriately inserting one or more gaps thereto, so that the base at the same position as 917nt in wild type GRIA1 cDNA is identified as the corresponding base in the variant gene. The single base substitution identified in Examples below may also be hereinafter referred to as "base substitution at 917nt" in the present specification.

It should be understood, however, that (a) mutation(s) which can be used as an index in the present invention is(are) not restricted to those described above. Any mutations can be used as an index in the method of the present invention, as long as the mutation may decrease or diminish the channel activity of GRIA1. The cDNA sequence of bovine wild type GRIA1 gene is shown in SEQ ID NO:1 in SEQUENCE LISTING, and the codons encoding for each amino acid are known. The channel activity of GRIA1 can be easily assessed by a conventional method as described above. Therefore, the mutation resulting in an abnormal GRIA1 are not restricted to the base substitution identified in Examples below.

Whether GRIA1 gene has at least one mutation which results in an abnormal GRIA1 or not can be examined by using a well-known technique in the art. For example, a nucleic acid sample obtained from a bovine by a conventional well-known method may be examined for the existence of the at least one mutation in the coding region of GRIA1 gene by a conventional method, so that the existence of the mutation(s) resulting in an abnormal GRIA1 can be confirmed. The existence of the mutation(s) in GRIA1 gene may also be confirmed by examining a protein sample obtained from a bovine by a conventional well-known method for the existence of an abnormal GRIA1 by using an antibody specifically recognizing an abnormal GRIA1, which antibody can be prepared by a conventional method. In the present invention, the former method in which a nucleic acid sample is examined is preferred.

The nucleic acid sample is not restricted, and the sample may be a genomic DNA sample, an RNA sample (total RNA or mRNA), a cDNA sample or the like.

Specific examples of the method in which a nucleic acid sample is examined for the existence of the above-described mutation in GRIA1 gene include, for example, a method in which the nucleic acid sample is subjected to nucleic acid amplification reaction and the existence of the mutation is determined based on the base sequence of the amplification product. As the nucleic acid amplification reaction, a well-known method such as PCR or the like can be preferably used. The existence of the mutation may also be confirmed by a method in which a region comprising the above-described mutation is amplified and then the amplification product is sequenced; or, in cases where the mutation creates difference in restriction pattern between normal and abnormal sequences, by a method in which the restriction fragment length polymorphism of the amplification product is analyzed (i.e. the well-known PCR-RFLP method). All these methods mentioned above are included in a method in which the existence of the mutation is determined "based on the base sequence of the amplification product". Alternatively, the existence of the mutation may also be determined based on whether the amplification occurs or not by using a primer which is targeted to the mutation site. Those skilled in the art can easily design and prepare such a primer, depending on the modes of the mutations. For example, in cases where the mutation an abnormal GRIA1 gene has is deletion mutation, the primer can be designed such that 3'-end region of the primer hybridizes with the region which is deleted in an abnormal GRIA1 gene. When such the primer is used, the amplification product can be obtained if the nucleic acid sample contains normal GRIA1 gene, while the amplification product cannot be obtained if the nucleic acid sample contains homozygous abnormal GRIA1 gene. Thus the existence of the above-described mutation can be determined based on whether the amplification occurs or not.

It is easy for those skilled in the art to design and prepare the primer used in the above-described nucleic acid amplification reaction, referring to SEQ ID NO:1 or NO:5, using a commercially available nucleic acid synthesizer or the like, by a conventional method. Specifically, the primer can be designed by referring to SEQ ID NO:1 in cases where the sample is RNA or cDNA, and by referring to SEQ ID NO:5 in cases where the sample is genomic DNA. SEQ ID NO:5 is the sequence of Exon 7 and a part of its flanking introns. The 4342nt-4509nt region of SEQ ID NO:5 is Exon 7, where the point mutation identified in Examples below exists. The primer which can detect the mutation in Exon 7 by using a genomic DNA sample may be easily designed by referring to SEQ ID NO:5. The nucleic acid amplification reaction per se such as PCR is well known, and kits and apparatuses therefor are commercially available, so that it may easily be carried out by using them.

The length of the primer is not restricted, and usually about 18 to 50 bases, preferably 18 to 35 bases. The primer may be labeled with an enzyme (e.g. peroxidase, alkaline phosphatase), isotope (e.g. $^{32}P$), biotin, fluorescent dye, luminescent substance, coloring substance or the like. The amplification will be time-consuming if the size of the amplification product is too large, and therefore the size is preferably not more than about 3000 bp, more preferably not more than about 1500 bp. Particularly, in cases where the amplification product is sequenced, the size of the amplification product is preferably not more than about 1000 bp, more preferably not more than about 500 bp, in view of accurate sequencing of the mutation site. On the other hand, the lower limit of the amplification product is preferably not less than about 50 bp, in view of easier investigation of, for example, whether the amplification occurs or not by electrophoresis or the like.

For example, in cases where whether the above-described mutation exists or not is determined based on the base sequence of the amplification product, a forward primer and a reverse primer which specifically hybridize with partial regions upstream and downstream of the mutation site, respectively, may be used to amplify the region containing the mutation site. For example, in cases where a genomic DNA sample is examined for the existence of the single base substitution identified in Examples below, the forward primer may be a primer specifically hybridizing with a partial region located in 1nt-4396nt region of the base sequence shown in SEQ ID NO:5, and the reverse primer may be a primer specifically hybridizing with a partial region located in 4398nt-13161nt region of the base sequence shown in SEQ ID NO:5. In cases where an RNA or cDNA sample is examined, the forward primer may be a primer specifically hybridizing with a partial region located in 1nt-916nt region of the base sequence shown in SEQ ID NO:1, and the reverse primer may be a primer specifically hybridizing with a partial region located in 918nt-2721nt region of the base sequence shown in SEQ ID NO:1.

In the present specification and claims, the term "partial region" refers to a region consisting of a part of the base sequence shown in SEQ ID NO:1 or NO:5. A "partial region" preferably consists of not less than 18 consecutive bases. It is understood that a "region" or "partial region" of a certain base sequences as used herein includes, unless otherwise apparent from the context, not only the base sequence per se expressly written in the SEQUENCE LISTING, but also the sequence complementary thereto. For example, the phrase "a primer specifically hybridizing with a partial region of the base sequence shown in SEQ ID NO:5" includes not only a primer hybridizing with a part of the base sequence shown in SEQ ID NO:5, but also one hybridizing with a base sequence complementary to a part of the base sequence shown in SEQ ID NO:5. Those skilled in the art can easily understand, based on the common technical knowledge and the context of the present specification and claims, which base sequence is referred to by the term "region" or "partial region".

The term "specifically hybridize" means that a certain sequence hybridizes only with the subject region and does not substantially hybridize with the other regions under ordinary hybridization conditions. The term "ordinary hybridization condition" refers to a condition used for annealing in the ordinary PCR or the ordinary detection with probes. For example, in cases of PCR with Taq polymerase, the term refers to a reaction condition at an appropriate annealing temperature of about 54° C. to 60° C. using a common buffer such as one containing 50 mM KCl, 10 mM Tris-HCl (pH 8.3 to 9.0) and 1.5 mM $MgCl_2$. In cases of Northern hybridization, the term refers to a reaction condition at an appropriate hybridization temperature of 42° C. to 65° C. using a common hybridization solution such as one containing 5×SSPE, 50% formamide, 5×Denhardt's solution and 0.1 to 0.5% SDS. It should be noted, however, that the appropriate annealing temperature and hybridization temperature are not restricted to those exemplified above, and may be determined based on Tm of the primer or the probe and on the empirical rules. Those skilled in the art can easily determine the appropriate temperature. The term "does not substantially hybridize" means that a hybridization does not occur at all or, even if it occurs, the degree of the hybridization with regions other than the subject region is considerably lower than that of the hybridization with the subject region so that the hybridization with other regions can be relatively ignored.

Although the primers which specifically hybridizes under such conditions preferably have the sequence entirely complementary to the partial region with which the primer hybridizes, in most cases the hybridization with the subject partial region and the subsequent amplification can usually occur if the primer having the same sequence as the complementary sequence except that not more than about 10% of the bases is substituted. It is also well-known in the art that primers comprising at its 5'-end any arbitrary additional sequence such as restriction enzyme recognition sequence can specifically hybridize with the subject partial region and amplify the desired region.

Therefore, in cases where a genomic DNA sample is examined for the existence of the base substitution mutation at 917nt, not only primers having a sequence of not less than 18 consecutive bases selected from 1nt-4396nt region of the base sequence shown in SEQ ID NO:5, but also primers having the same sequence as the consecutive bases in the 1nt-4396nt region mentioned above except that not more than 10% of the consecutive bases is substituted may be used as the forward primer. Furthermore, primers having the same sequence as either of these primers except that an additional sequence is attached to its 5'-end may also be used as the forward primer. That is, as the above-described forward primer, those comprising at its 3'-end (i) a sequence of not less than 18 consecutive bases selected from 1nt-4396nt region of the base sequence shown in SEQ ID NO:5, or (ii) the same sequence as the above-mentioned consecutive bases selected from the 1nt-4396nt region except that not more than 10% of the consecutive bases is substituted may be used. Similarly, as the reverse primer, not only primers having a sequence complementary to not less than 18 consecutive bases selected from the 4398nt-13161nt region of the base sequence shown in SEQ ID NO:5, but also primers having the same sequence as the above-mentioned sequence complementary to the consecutive bases selected from 4398nt-13161nt region except that not more than 10% of the bases constituting the complementary sequence is substituted may be used. Furthermore, primers having the same sequence as either of these primers except that an additional sequence is attached to its 5'-end may also be used as the reverse primer. That is, as the above-mentioned reverse primer, those comprising at its 3'-end (i) a sequence complementary to not less than 18 consecutive bases selected from 4398nt-13161nt region of the base sequence shown in SEQ ID NO:5, or (ii) the same sequence as the above-mentioned sequence complementary to the consecutive bases selected from 4398nt-13161nt region except that not more than 10% of the bases constituting the complementary sequence is substituted may be used. It is preferred that the above-mentioned primers having "the same sequence except that not more than 10% of the bases is substituted" should have such substitution(s) at any position(s) except its 3'-end base.

Among these, as the forward primer used for checking the base substitution at 917nt in a genomic DNA sample, especially preferred are those comprising at its 3'-end the sequence of not less than 18 consecutive bases selected from 1nt-4396nt region of the base sequence shown in SEQ ID NO:5, and those having the same sequence as not less than 18 consecutive bases selected from the 1nt-4396nt region except that not more than 10% of the consecutive bases is substituted. Specific examples of such the preferred forward primer include, but not limited to, the primer having the base sequence shown in SEQ ID NO:3 as used in Examples below.

As the reverse primer used for checking the base substitution at 917nt in a genomic DNA sample, more preferred are those comprising at its 3'-end a sequence complementary to not less than 18 consecutive bases selected from 4398nt-13161nt region of the base sequence shown in SEQ ID NO:5, and those having the same sequence as the sequence complementary to the consecutive bases selected from 4398nt-13161nt region except that not more than 10% of the bases constituting the complementary sequence is substituted. Among these, still more preferred are those having a sequence complementary to not less than 18 consecutive bases selected from 4398nt-13161nt region of the base sequence shown in SEQ ID NO:5. Specific examples of such the preferred reverse primer include, but not limited to, the primer having the base sequence shown in SEQ ID NO:4 as used in Examples below.

In cases where an RNA or cDNA sample is used for checking the base substitution at 917nt, primers comprising at its 3'-end (i) a sequence of not less than 18 consecutive bases selected from 1nt-916nt region of the base sequence shown in SEQ ID NO:1, or (ii) the same sequence as the consecutive bases selected from the 1nt-916nt region except that not more than 10% of the consecutive bases is substituted may be used as the forward primer, and primers comprising at its 3'-end (i) a sequence complementary to not less than 18 consecutive bases selected from 918nt-2721nt region of the base sequence shown in SEQ ID NO:1, or (ii) the same sequence as the sequence complementary to the consecutive bases selected from the 918nt-2721nt region except that not more than 10% of the bases constituting the complementary sequence is substituted may be used as the reverse primer. Among these, more preferred forward primers are those comprising at its 3'-end a sequence of not less than 18 consecutive bases selected from 1nt-916nt region of the base sequence shown in SEQ ID NO:1, and those having the same sequence as the consecutive bases selected from the 1nt-916nt region except that not more than 10% of the consecutive bases is substituted. Among these, especially preferred are those having a sequence of not less than 18 consecutive bases selected from the 1nt-916nt region of the base sequence shown in SEQ ID NO:1. Meanwhile, more preferred reverse primers are those comprising at its 3'-end a sequence complementary to not less than 18 consecutive sequence selected from the above-mentioned 918nt-2721nt region, and those having the same sequence as the sequence complementary to the consecutive bases selected from the above-mentioned 918nt-2721nt region except that not more than 10% of the bases constituting the complementary sequence is substituted. Among these, especially preferred are those having a sequence complementary to not less than 18 consecutive bases selected from the 918nt-2721nt region.

In the present specification and claims, the term "have the base sequence" means that the bases are aligned in the order described. Thus, for example, "the primer having the base sequence shown in SEQ ID NO:3" means the primer having a size of 20 bases whose sequence is "agcctcccta ccagctctct" as shown in SEQ ID NO:3. The term "have the amino acid sequence" is construed in the same manner.

In addition to the method utilizing a nucleic acid amplification reaction, examples of the method in which a nucleic acid sample is used include Southern hybridization in which a genomic DNA sample is used, and Northern hybridization in which an RNA sample is used. In these methods, for example, a probe which specifically hybridizes with a sequence encoding a normal GRIA1 but does not hybridize with a mutant sequence encoding an abnormal GRIA1 can be used for checking the existence of the mutation. Those skilled in the art can easily prepare such a probe, depending on the modes of the mutations, referring to the wild type sequence shown in SEQ ID NO:1 or NO:5.

The length of the probes used in the hybridization methods is preferably not less than 18 bases, more preferably not less than 20 bases, in view of assuring specificity. The upper limit of the length of the probes is preferably not more than the full length of SEQ ID NO:1 in cases where the nucleic acid sample is RNA or cDNA. Although it is preferred that the probes specifically hybridizing with the desired partial region have the same sequence as the desired partial region, those having a certain sequence identity (e.g. not less than 80%, preferably not less than 90%, more preferably not less than 95%, still more preferably not less than 98% identity) to the desired subject partial region may be used, as such primers can also specifically hybridize with the subject partial region. However, in cases where it is desired to distinguish an abnormal sequence from a normal sequence based on whether the hybridization occurs or not, the sequence identity should be sufficiently high, e.g. 98% to 100%, if there is less difference between normal and abnormal sequences. Those skilled in the art can easily design and prepare an appropriate probe, depending on the modes of the mutations the abnormal sequence has, referring to SEQ ID NO:1 or NO:5.

The primers specifically hybridizing with a partial region of the base sequence shown in SEQ ID NO:1 or NO:5 which are used in the above-described method utilizing the nucleic acid amplification reaction may be provided as a reagent for determining efficiency of ovum collection in bovine. The reagent may comprise only the primer, or may be in the form of a solution in which the primer is dissolved in a buffer, or may be provided as a set comprising the dried primer and a buffer. The reagent may further comprise various additives such as stabilizer and the like. Preferred examples of the primer contained in the reagent are the same as hereinabove described in connection with the method of the present invention.

The present invention further provides a kit for carrying out the method of the present invention in which a nucleic acid amplification reaction is used. The kit comprises a primer set, each primer of which set specifically hybridizes with a partial region of the base sequence shown in SEQ ID NO:1 or NO:5. Preferred examples of the primer contained in the kit are the same as hereinabove described in connection with the method of the present invention. The primers in the kit may be in various forms similarly to the reagent described above.

EXAMPLES

The present invention will now be described more concretely by way of an example thereof. However, the present invention is not restricted to the example below. Unless otherwise specified, the experiments below were carried out according to the method described in J. Sambrook & D. W. Russell (Ed.), Molecular cloning, a laboratory manual (3rd edition), Cold Spring Harbor Press, Cold Spring Harbor, N.Y. (2001), or variations or modifications thereof. The commercially available reagent kits and apparatuses were used, otherwise specified, in accordance with the instructions attached thereto.

1. Identification of Gene Mutation Involved in Efficiency of Ovum Collection in Bovine (1) Sequencing of Bovine GRIA1 Gene A pedigree of Japanese Black Cattle was investigated using 1020 DNA markers which covered all the chromosomes with showing polymorphisms so that the chromosomal region linked to the efficiency of ovum collection was identified. The bovine pedigree herein used was composed of 67 bovines with a high efficiency from which 16.6 or more ova on an average per single superovulatory treatment could be collected, and 67 bovines with a low efficiency from which 7.8 or less on an average per single superovulatory treatment could be collected. As a result, chromosome VII showed strong linkage. Chromosome VII was then further subjected to a linkage analysis using an additional 89 markers to identify 287 kb region related to control of efficiency of ovum collection (hereinafter referred to as "ovum collection control region"), which region contained GRIA1 gene. The coding region of GRIA1 gene in both bovines (high efficiency and low efficiency) was sequenced and compared to find that bovines with a low efficiency had a specific amino acid mutation.

(2) Influence of Amino Acid Mutation on Function of GRIA1

GRIA1 gene encodes an ion channel protein. To investigate the function of GRIA1 gene, GRIA1 gene was introduced into frog oocytes to express it therein and a membrane current after the glutamic acid stimulation was measured by a conventional method. The channel activity of GRIA1 encoded by each GRIA1 gene was evaluated based on the value of 50% effective concentration ($EC_{50}$). $EC_{50}$ was the concentration of glutamic acid at which the membrane current was measured at 50% level, regarding the membrane current measured at 300 μM glutamic acid as 100%.

As a result, $EC_{50}$ of the mutant (abnormal) GRIA1 gene the low efficiency bovines had was higher than that of normal GRIA1 gene the high efficiency bovines had, i.e., the channel activity of an abnormal GRIA1 derived from the low efficiency bovines was lower than that of a normal GRIA1. This result suggests that the reduced channel activity of the mutated GRIA1 leads to the low efficiency of ovum collection.

(3) Influence of GRIA1 Gene Mutation on Ovary Under Superovulatory Treatment

To investigate influence of GRIA1 gene on ovary, the number of immature and mature ovarian follicles before and after the superovulatory treatment was counted in 6 bovines having normal GRIA1 gene and 4 bovines having abnormal GRIA1 gene. As a result, compared to bovines having abnormal GRIA1 gene, bovines having normal GRIA1 gene had more immature follicles before the superovulatory treatment, and also developed more mature follicles after the superovulatoly treatment (Table 1). This result suggests that GRIA1 with reduced channel activity results in reduced number of immature follicles in the ovary before superovulatory treatment, which leads to reduction of mature follicles ready for ovulation.

TABLE 1

Influence of Mutation in GRIA1 Gene on Number of Follicles and Ovum Collection

| GRIA1 | Number of Bovines | Number of Immature Follicles Before Superovulatory treatment | Number of Mature Follicles After Superovulatory treatment |
|---|---|---|---|
| Normal | 6 | $20.2 \pm 0.5^a$ | $17.0 \pm 2.3^a$ |
| Abnormal | 4 | $10.8 \pm 1.2^b$ | $7.5 \pm 1.5^b$ | mean ± standard error
$a,b$ significant between different symbols (4) Influence of Mutation in GRIA1 Gene on Number of Ova Collected After Superovulatory Treatment To investigate influence of GRIA1 gene on the ovary, the number of the ova collected from 277 bovines with normal GRIA1 gene and 44 bovines with abnormal GRIA1 gene after superovulatory treatment was counted in the same manner as (3). As a result, the ova collected from the bovines with normal GRIA1 gene were significantly more than those collected from the bovines with abnormal GRIA1 gene (Table 2), which suggests that the efficiency of producing embryo from the superovulated ova is reduced in bovines with abnormal GRIA1 gene, compared to those with normal GRIA1 gene.

TABLE 2

Influence of Mutation in GRIA1 Gene on Number of Ova Collected After Superovulatory Treatment

| GRIA1 | Number of Bovines | Number of Collected Ova |
|---|---|---|
| Normal | 277 | 16.8 ± 8.6[a] |
| Abnormal | 44 | 11.1 ± 7.0[b] | mean ± standard error
[a,b]significant between different symbols

2. Determining Existence of GRIA1 Gene Mutation in Bovine Genomic DNA

Primers GRIA1-F and GRIA1-R, used for the amplification of DNA fragment containing the mutation site found in the low efficiency bovines, were synthesized. The base sequences of GRIA1-F and GRIA1-R are shown in SEQ ID NO:3 and NO:4 in SEQUENCE LISTING.

GRIA1-F: AGCCTCCCTA CCAGCTCTCT [SEQ ID NO: 3]

GRIA1-R: CGTTGTTGCC AGCCTCAC [SEQ ID NO: 4]

Genomic DNA was prepared from blood samples (containing EDTA or heparin as an anticoagulant) obtained from the bovines, using the automatic nucleic acid isolation system NA-1000 (produced by KURABO). Using these genomic DNAs as a template, PCR (a cycle of 94° C. for 20 sec, 60° C. for 30 sec and 72° C. for 1 min was repeated 35 times) was performed with DNA polymerase and primers GRIA1-F and GRIA1-R, and then PCR products were sequenced by 3730 fluorescent DNA sequencer (produced by Applied Biosystems) to compare the base sequences. As shown in FIG. 2, the 111th base in the PCR product was guanine (G) when the template was normal GRIA1 gene, while adenine (A) when the template was abnormal GRIA1 gene. Thus, an abnormal GRIA1 gene can be distinguished from a normal GRIA1 gene by confirming the base at this position.

This invention has been described in detail with particular reference to certain embodiments, but variations and modifications can be made without departing from the spirit and scope of the invention as defined in the following claims.

What is claimed is:

1. A method of predicting efficiency of ovum collection in a bovine comprising
    detecting a mutation that results in an abnormal GRIA1 protein wherein said detecting comprises detecting in a nucleic acid sample the presence of an adenine at nucleotide 917 of SEQ ID NO: 1 or said detecting comprises detecting in a protein sample the presence of an asparagine at position 306 of SEQ ID NO: 2, and
    predicting that the bovine with said adenine or said asparagine will have lower ovum production efficiency than if a guanine were present at that position in SEQ ID NO: 1 or if a serine were present at that position in SEQ ID NO: 2.

2. The method according to claim 1, wherein which comprises detecting the presence of the asparagine at position 306 of SEQ ID NO: 2.

3. The method according to claim 1, wherein which comprises detecting the presence of an adenine at nucleotide 917 of SEQ ID NO: 1.

4. The method according to claim 1, wherein a nucleic sample is obtained from the bovine and the nucleotide present at position 917 of SEQ ID NO: 1 is detected.

5. The method according to claim 4, which comprises:
    subjecting said nucleic acid sample to nucleic acid amplification, and
    detecting the presence of said mutation based on whether the amplification occurs or not or on the base sequence of the amplification product.

6. The method according to claim 5, wherein the presence of said mutation is determined based on the base sequence of the amplification product.

7. The method according to claim 6, which comprises amplifying a region containing said mutation in said nucleic acid sample by using a primer set, each primer of said set specifically hybridizing with a partial region of the base sequence shown in SEQ ID NO:1 or NO:5.

8. The method according to claim 7, wherein said mutation is the base substitution of guanine at 917nt in GRIA1 gene cDNA to adenine, and wherein a region comprising the base at 917nt in a genome DNA sample is amplified by using the primer set, each primer of said set specifically hybridizing with a partial region of the base sequence shown in SEQ ID NO:5.

9. The method according to claim 8, wherein said primer set comprises a forward primer which specifically hybridizes with a first partial region located in 1nt-4396nt region of the base sequence shown in SEQ ID NO:5, and a reverse primer which specifically hybridizes with a second partial region located in 4398nt-13161nt region of the base sequence shown in SEQ ID NO:5.

10. The method according to claim 9, wherein:
    said forward primer comprises at its 3'-end (i) a sequence of not less than 18 consecutive bases selected from 1nt-4396nt region of the base sequence shown in SEQ ID NO:5, or (ii) the same sequence as said consecutive bases selected from said 1nt-4396nt region except that not more than 10% of said consecutive bases is substituted; and said reverse primer comprises at its 3'-end (i) a sequence complementary to not less than 18 consecutive bases selected from 4398nt-13161nt region of the base sequence shown in SEQ ID NO:5, or (ii) the same sequence as said sequence complementary to said consecutive bases selected from 4398nt-13161nt region except that not more than 10% of the bases constituting said complementary sequence is substituted.

11. The method according to claim 10, wherein said forward primer comprises at its 3'-end the sequence of not less than 18 consecutive bases selected from 1nt-4396nt region of the base sequence shown in SEQ ID NO:5; and said reverse primer comprises at its 3'-end a sequence complementary to not less than 18 consecutive bases selected from 4398nt-13161nt region of the base sequence shown in SEQ ID NO:5.

12. The method according to claim 10, wherein:

said forward primer has (i) a sequence of not less than 18 consecutive bases selected from 1nt-4396nt region of the base sequence shown in SEQ ID NO:5, or (ii) the same sequence as said consecutive bases selected from said 1nt-4396nt region except that not more than 10% of said consecutive bases is substituted; and said reverse primer has (i) a sequence complementary to not less than 18 consecutive bases selected from 4398nt-13161nt region of the base sequence shown in SEQ ID NO:5, or (ii) the same sequence as said sequence complementary to said consecutive bases selected from 4398nt-13161nt region except that not more than 10% of the bases constituting said complementary sequence is substituted.

13. The method according to claim 12, wherein said forward primer has a sequence of not less than 18 consecutive bases selected from 1nt-4396nt region of the base sequence shown in SEQ ID NO:5; and said reverse primer has a sequence complementary to not less than 18 consecutive bases selected from 4398nt-13161nt region of the base sequence shown in SEQ ID NO:5.

14. The method according to claim 13, wherein said forward primer has the base sequence shown in SEQ ID NO:3 and said reverse primer has the base sequence shown in SEQ ID NO:4.

* * * * *

SEQUENCE LISTING

```
<160> NUMBER OF SEQ ID NOS: 5

<210> SEQ ID NO 1
<211> LENGTH: 2721
<212> TYPE: DNA
<213> ORGANISM: Bos taurus
<220> FEATURE:
<221> NAME/KEY: CDS
<222> LOCATION: (1)..(2721)
<223> OTHER INFORMATION:

<400> SEQUENCE: 1 atg cag cac att ttt gcc ttc ttc tgc acc ggt ttc cta ggc gcg gta      48
Met Gln His Ile Phe Ala Phe Phe Cys Thr Gly Phe Leu Gly Ala Val
1               5                   10                  15 gta ggt gcc aat ttc ccc aac aat atc cag atc ggg gga tta ttt cca      96
Val Gly Ala Asn Phe Pro Asn Asn Ile Gln Ile Gly Gly Leu Phe Pro
            20                  25                  30 aac cag cag tca cag gaa cat gct gct ttt aga ttt gct ttg tca caa     144
Asn Gln Gln Ser Gln Glu His Ala Ala Phe Arg Phe Ala Leu Ser Gln
        35                  40                  45 ctc aca gag ccc cca aag ttg ctc ccc cag att gat att gtg aac atc     192
Leu Thr Glu Pro Pro Lys Leu Leu Pro Gln Ile Asp Ile Val Asn Ile
    50                  55                  60 agc gac agc ttt gag atg acc tac aga ttc tgt tcc cag ttc tct aaa     240
Ser Asp Ser Phe Glu Met Thr Tyr Arg Phe Cys Ser Gln Phe Ser Lys
65                  70                  75                  80 gga gtc tat gcc atc ttt ggg ttt tat gaa cgg agg act gtc aac atg     288
Gly Val Tyr Ala Ile Phe Gly Phe Tyr Glu Arg Arg Thr Val Asn Met
                85                  90                  95 ctg acc tcc ttc tgc ggg gcc ctc cac gtc tgc ttc att aca cca agc     336
Leu Thr Ser Phe Cys Gly Ala Leu His Val Cys Phe Ile Thr Pro Ser
            100                 105                 110 ttt ccc gtt gac aca tcc aac cag ttt gtc ctc cag ctg cgc ccc gag     384
Phe Pro Val Asp Thr Ser Asn Gln Phe Val Leu Gln Leu Arg Pro Glu
        115                 120                 125 ctg cag gat gcc ctc atc agt atc atc gac cat tac aag tgg caa aaa     432
Leu Gln Asp Ala Leu Ile Ser Ile Ile Asp His Tyr Lys Trp Gln Lys
```

```
                130                     135                     140
ttt gtc tac att tat gat gct gac cgg ggt ctg tcc gtc ttg cag aaa       480
Phe Val Tyr Ile Tyr Asp Ala Asp Arg Gly Leu Ser Val Leu Gln Lys
145                     150                     155                 160 gtc ctg gac aca gct gct gag aag aac tgg cag gtg aca gcc gtg aac       528
Val Leu Asp Thr Ala Ala Glu Lys Asn Trp Gln Val Thr Ala Val Asn
                    165                     170                     175 att ttg aca acc acg gag gag ggt tac cgg atg ctc ttc cag gac ctg       576
Ile Leu Thr Thr Thr Glu Glu Gly Tyr Arg Met Leu Phe Gln Asp Leu
                180                     185                     190 gag aag aaa aag gag cgg ctg gtg gtg gtg gac tgt gaa tca gaa cgc       624
Glu Lys Lys Lys Glu Arg Leu Val Val Val Asp Cys Glu Ser Glu Arg
            195                     200                     205 ctc aat gct atc ctg ggc cag att gta aag ctg gag aag aat ggc att       672
Leu Asn Ala Ile Leu Gly Gln Ile Val Lys Leu Glu Lys Asn Gly Ile
        210                     215                     220 ggc tac cac tat atc ctt gca aat ctg ggt ttc atg gac att gac tta       720
Gly Tyr His Tyr Ile Leu Ala Asn Leu Gly Phe Met Asp Ile Asp Leu
225                     230                     235                 240 aac aaa ttc aag gag agt gga gca aac gta aca ggt ttc cag ttg gtg       768
Asn Lys Phe Lys Glu Ser Gly Ala Asn Val Thr Gly Phe Gln Leu Val
                    245                     250                     255 aac tac aca gac acc atc ccg gcc aag atc atg caa cag tgg aag aac       816
Asn Tyr Thr Asp Thr Ile Pro Ala Lys Ile Met Gln Gln Trp Lys Asn
                260                     265                     270 agt gat gct cgg gac cac acc cgg gtg gac tgg aag aga cct aag tac       864
Ser Asp Ala Arg Asp His Thr Arg Val Asp Trp Lys Arg Pro Lys Tyr
            275                     280                     285 acc tct gcg ctc acc tac gat ggg gtg aag gtg atg gct gag gct ttc       912
Thr Ser Ala Leu Thr Tyr Asp Gly Val Lys Val Met Ala Glu Ala Phe
        290                     295                     300 cag agc ctg cgg agg cag aga att gat atc tcc cgc cgg ggg aat gct       960
Gln Ser Leu Arg Arg Gln Arg Ile Asp Ile Ser Arg Arg Gly Asn Ala
305                     310                     315                 320 ggg gac tgc ctg gct aac cca gct gtg ccc tgg ggc cag ggc atc gac      1008
Gly Asp Cys Leu Ala Asn Pro Ala Val Pro Trp Gly Gln Gly Ile Asp
                    325                     330                     335 atc cag aga gct ctg cag cag gtg cgg ttt gaa ggc ttg aca gga aat      1056
Ile Gln Arg Ala Leu Gln Gln Val Arg Phe Glu Gly Leu Thr Gly Asn
                340                     345                     350 gtg caa ttt aat gag aaa gga cgg cgg acc aac tac acc ctc cac gtg      1104
Val Gln Phe Asn Glu Lys Gly Arg Arg Thr Asn Tyr Thr Leu His Val
            355                     360                     365 att gaa atg aag cat gat ggc atc cga aag att ggc tac tgg aat gaa      1152
Ile Glu Met Lys His Asp Gly Ile Arg Lys Ile Gly Tyr Trp Asn Glu
        370                     375                     380 gat gac aaa ttc gtc cct gca gcc acg gat gct caa gcc ggg ggg gat      1200
Asp Asp Lys Phe Val Pro Ala Ala Thr Asp Ala Gln Ala Gly Gly Asp
385                     390                     395                 400 aac tca agt gtc cag aat aga aca tac atc gtc act aca atc cta gaa      1248
Asn Ser Ser Val Gln Asn Arg Thr Tyr Ile Val Thr Thr Ile Leu Glu
                    405                     410                     415 gat cct tat gtg atg ctc aag aag aat gcc aac cag ttt gaa ggc aat      1296
Asp Pro Tyr Val Met Leu Lys Lys Asn Ala Asn Gln Phe Glu Gly Asn
                420                     425                     430 gac cgc tac gag ggc tac tgt gtg gag ttg gcg gca gag att gcc aag      1344
Asp Arg Tyr Glu Gly Tyr Cys Val Glu Leu Ala Ala Glu Ile Ala Lys
            435                     440                     445 cat gtg gga tat tcc tac cgt ctt gag att gtc agc gat gga aaa tat      1392
His Val Gly Tyr Ser Tyr Arg Leu Glu Ile Val Ser Asp Gly Lys Tyr
```

-continued

| | | |
|---|---|---|
| 450 | 455 | 460 |

| | |
|---|---|
| gga gcc cgt gac cct gac aca aag gct tgg aat ggc atg gtg gga gag<br>Gly Ala Arg Asp Pro Asp Thr Lys Ala Trp Asn Gly Met Val Gly Glu<br>465                    470                    475                    480 | 1440 |
| ctg gtc tat gga aga gca gat gtg gct gtt gcc cct tta act atc acc<br>Leu Val Tyr Gly Arg Ala Asp Val Ala Val Ala Pro Leu Thr Ile Thr<br>                    485                    490                    495 | 1488 |
| ttg gtc cgg gaa gag gtg atc gat ttc tcc aag ccg ttt atg agt ctg<br>Leu Val Arg Glu Glu Val Ile Asp Phe Ser Lys Pro Phe Met Ser Leu<br>            500                    505                    510 | 1536 |
| ggg atc tcc atc atg ata aaa aag cca cag aag tcc aaa ccg ggg gtc<br>Gly Ile Ser Ile Met Ile Lys Lys Pro Gln Lys Ser Lys Pro Gly Val<br>                515                    520                    525 | 1584 |
| ttt tcc ttc ctg gat cct ttg gct tat gag atc tgg atg tgc att gtg<br>Phe Ser Phe Leu Asp Pro Leu Ala Tyr Glu Ile Trp Met Cys Ile Val<br>530                      535                    540 | 1632 |
| ttc gcc tac att gga gtg agc gtc gtc ctt ttc ctg gtc agc cgt ttc<br>Phe Ala Tyr Ile Gly Val Ser Val Val Leu Phe Leu Val Ser Arg Phe<br>545                    550                    555                    560 | 1680 |
| agc ccc tac gaa tgg cac agc gaa gag ttt gag gaa ggg cga gac caa<br>Ser Pro Tyr Glu Trp His Ser Glu Glu Phe Glu Glu Gly Arg Asp Gln<br>                565                    570                    575 | 1728 |
| acc acc agc gac cag tcc aat gag ttt ggg ata ttc aac agc ttg tgg<br>Thr Thr Ser Asp Gln Ser Asn Glu Phe Gly Ile Phe Asn Ser Leu Trp<br>            580                    585                    590 | 1776 |
| ttc tcc ctg gga gcc ttc atg cag caa gga tgt gac atc tct ccc agg<br>Phe Ser Leu Gly Ala Phe Met Gln Gln Gly Cys Asp Ile Ser Pro Arg<br>                595                    600                    605 | 1824 |
| tcc ttg tcc ggc cgc atc gtg ggc ggc gtc tgg tgg ttc ttc acc ttg<br>Ser Leu Ser Gly Arg Ile Val Gly Gly Val Trp Trp Phe Phe Thr Leu<br>610                      615                    620 | 1872 |
| atc atc atc tcc tcc tac aca gcc aac ctg gcc gcc ttc ctg aca gtg<br>Ile Ile Ile Ser Ser Tyr Thr Ala Asn Leu Ala Ala Phe Leu Thr Val<br>625                      630                    635                    640 | 1920 |
| gag agg atg gtg tct ccc atc gag agt gct gag gac cta gca aag cag<br>Glu Arg Met Val Ser Pro Ile Glu Ser Ala Glu Asp Leu Ala Lys Gln<br>                    645                    650                    655 | 1968 |
| aca gaa atc gct tac ggg acc cta gaa gcg gga tct acg aag gag ttc<br>Thr Glu Ile Ala Tyr Gly Thr Leu Glu Ala Gly Ser Thr Lys Glu Phe<br>            660                    665                    670 | 2016 |
| ttc agg agg tct aaa atc gcc gtg ttt gag aag atg tgg acg tac atg<br>Phe Arg Arg Ser Lys Ile Ala Val Phe Glu Lys Met Trp Thr Tyr Met<br>                675                    680                    685 | 2064 |
| aag tca gca gag cca tcc gtg ttt gtg cgg acc aca gag gag ggg atg<br>Lys Ser Ala Glu Pro Ser Val Phe Val Arg Thr Thr Glu Glu Gly Met<br>690                      695                    700 | 2112 |
| atc cga gta agg aaa tcc aaa ggc aaa tac gcc tac ctt cta gag tcc<br>Ile Arg Val Arg Lys Ser Lys Gly Lys Tyr Ala Tyr Leu Leu Glu Ser<br>705                      710                    715                    720 | 2160 |
| acc atg aat gag tac att gag cag cgg aaa ccc tgt gac acc atg aag<br>Thr Met Asn Glu Tyr Ile Glu Gln Arg Lys Pro Cys Asp Thr Met Lys<br>                725                    730                    735 | 2208 |
| gtg gga ggt aac ttg gat tcc aaa ggc tat ggc att gca acg ccc aag<br>Val Gly Gly Asn Leu Asp Ser Lys Gly Tyr Gly Ile Ala Thr Pro Lys<br>            740                    745                    750 | 2256 |
| ggg tcc gcc ctg aga ggt ccc gta aac cta gcg gtt ttg aaa ctc agt<br>Gly Ser Ala Leu Arg Gly Pro Val Asn Leu Ala Val Leu Lys Leu Ser<br>                755                    760                    765 | 2304 |
| gag caa ggc gtc tta gac aag ctg aaa agc aaa tgg tgg tac gat aaa<br>Glu Gln Gly Val Leu Asp Lys Leu Lys Ser Lys Trp Trp Tyr Asp Lys | 2352 |

```
                        770                 775                 780
ggg gaa tgt gga agc aag gac tcc gga agt aag gac aag acc agt gct       2400
Gly Glu Cys Gly Ser Lys Asp Ser Gly Ser Lys Asp Lys Thr Ser Ala
785                 790                 795                 800 ctc agc ctc agc aat gtg gcg ggc gtg ttc tac atc ctg atc gga gga       2448
Leu Ser Leu Ser Asn Val Ala Gly Val Phe Tyr Ile Leu Ile Gly Gly
                    805                 810                 815 ctt gga ctc gcc atg ctg gtt gcc tta att gag ttc tgc tac aaa tcc       2496
Leu Gly Leu Ala Met Leu Val Ala Leu Ile Glu Phe Cys Tyr Lys Ser
            820                 825                 830 cgt agc gaa tcc aag cgg atg aag ggt ttc tgt ttg atc cca cag caa       2544
Arg Ser Glu Ser Lys Arg Met Lys Gly Phe Cys Leu Ile Pro Gln Gln
        835                 840                 845 tcc atc aat gaa gcc ata cgg aca tcg acg ctc ccc cga aac agt ggg       2592
Ser Ile Asn Glu Ala Ile Arg Thr Ser Thr Leu Pro Arg Asn Ser Gly
    850                 855                 860 gca gga gcc agc ggt gcc ggg agt gga gag aac ggc cgg gta gtc agc       2640
Ala Gly Ala Ser Gly Ala Gly Ser Gly Glu Asn Gly Arg Val Val Ser
865                 870                 875                 880 cat gac ttc ccc aag tcc atg caa tcg atc ccc tgc atg agc cac agt       2688
His Asp Phe Pro Lys Ser Met Gln Ser Ile Pro Cys Met Ser His Ser
                    885                 890                 895 tca ggg atg ccc ttg gga gcc act gga ttg taa                           2721
Ser Gly Met Pro Leu Gly Ala Thr Gly Leu
            900                 905

<210> SEQ ID NO 2
<211> LENGTH: 906
<212> TYPE: PRT
<213> ORGANISM: Bos taurus

<400> SEQUENCE: 2

Met Gln His Ile Phe Ala Phe Cys Thr Gly Phe Leu Gly Ala Val
1               5                   10                  15

Val Gly Ala Asn Phe Pro Asn Asn Ile Gln Ile Gly Gly Leu Phe Pro
            20                  25                  30

Asn Gln Gln Ser Gln Glu His Ala Ala Phe Arg Phe Ala Leu Ser Gln
        35                  40                  45

Leu Thr Glu Pro Pro Lys Leu Leu Pro Gln Ile Asp Ile Val Asn Ile
    50                  55                  60

Ser Asp Ser Phe Glu Met Thr Tyr Arg Phe Cys Ser Gln Phe Ser Lys
65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
            100                 105                 110

Phe Pro Val Asp Thr Ser Asn Gln Phe Val Leu Gln Leu Arg Pro Glu
        115                 120                 125

Leu Gln Asp Ala Leu Ile Ser Ile Ile Asp His Tyr Lys Trp Gln Lys
    130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
            180                 185                 190

Glu Lys Lys Lys Glu Arg Leu Val Val Val Asp Cys Glu Ser Glu Arg
        195                 200                 205
```

```
Leu Asn Ala Ile Leu Gly Gln Ile Val Lys Leu Glu Lys Asn Gly Ile
    210                 215                 220
Gly Tyr His Tyr Ile Leu Ala Asn Leu Gly Phe Met Asp Ile Asp Leu
225                 230                 235                 240
Asn Lys Phe Lys Glu Ser Gly Ala Asn Val Thr Gly Phe Gln Leu Val
                245                 250                 255
Asn Tyr Thr Asp Thr Ile Pro Ala Lys Ile Met Gln Gln Trp Lys Asn
            260                 265                 270
Ser Asp Ala Arg Asp His Thr Arg Val Asp Trp Lys Arg Pro Lys Tyr
        275                 280                 285
Thr Ser Ala Leu Thr Tyr Asp Gly Val Lys Val Met Ala Glu Ala Phe
290                 295                 300
Gln Ser Leu Arg Arg Gln Arg Ile Asp Ile Ser Arg Arg Gly Asn Ala
305                 310                 315                 320
Gly Asp Cys Leu Ala Asn Pro Ala Val Pro Trp Gly Gln Gly Ile Asp
                325                 330                 335
Ile Gln Arg Ala Leu Gln Gln Val Arg Phe Glu Gly Leu Thr Gly Asn
            340                 345                 350
Val Gln Phe Asn Glu Lys Gly Arg Arg Thr Asn Tyr Thr Leu His Val
        355                 360                 365
Ile Glu Met Lys His Asp Gly Ile Arg Lys Ile Gly Tyr Trp Asn Glu
370                 375                 380
Asp Asp Lys Phe Val Pro Ala Ala Thr Asp Ala Gln Ala Gly Gly Asp
385                 390                 395                 400
Asn Ser Ser Val Gln Asn Arg Thr Tyr Ile Val Thr Thr Ile Leu Glu
                405                 410                 415
Asp Pro Tyr Val Met Leu Lys Lys Asn Ala Asn Gln Phe Glu Gly Asn
            420                 425                 430
Asp Arg Tyr Glu Gly Tyr Cys Val Glu Leu Ala Ala Glu Ile Ala Lys
        435                 440                 445
His Val Gly Tyr Ser Tyr Arg Leu Glu Ile Val Ser Asp Gly Lys Tyr
450                 455                 460
Gly Ala Arg Asp Pro Asp Thr Lys Ala Trp Asn Gly Met Val Gly Glu
465                 470                 475                 480
Leu Val Tyr Gly Arg Ala Asp Val Ala Val Ala Pro Leu Thr Ile Thr
                485                 490                 495
Leu Val Arg Glu Glu Val Ile Asp Phe Ser Lys Pro Phe Met Ser Leu
            500                 505                 510
Gly Ile Ser Ile Met Ile Lys Lys Pro Gln Lys Ser Lys Pro Gly Val
        515                 520                 525
Phe Ser Phe Leu Asp Pro Leu Ala Tyr Glu Ile Trp Met Cys Ile Val
530                 535                 540
Phe Ala Tyr Ile Gly Val Ser Val Val Leu Phe Leu Val Ser Arg Phe
545                 550                 555                 560
Ser Pro Tyr Glu Trp His Ser Glu Glu Phe Glu Glu Gly Arg Asp Gln
                565                 570                 575
Thr Thr Ser Asp Gln Ser Asn Glu Phe Gly Ile Phe Asn Ser Leu Trp
            580                 585                 590
Phe Ser Leu Gly Ala Phe Met Gln Gln Gly Cys Asp Ile Ser Pro Arg
        595                 600                 605
Ser Leu Ser Gly Arg Ile Val Gly Gly Val Trp Trp Phe Phe Thr Leu
610                 615                 620
Ile Ile Ile Ser Ser Tyr Thr Ala Asn Leu Ala Ala Phe Leu Thr Val
```

```
                625                 630                 635                 640
Glu Arg Met Val Ser Pro Ile Glu Ser Ala Glu Asp Leu Ala Lys Gln
                    645                 650                 655
Thr Glu Ile Ala Tyr Gly Thr Leu Glu Ala Gly Ser Thr Lys Glu Phe
                660                 665                 670
Phe Arg Arg Ser Lys Ile Ala Val Phe Glu Lys Met Trp Thr Tyr Met
            675                 680                 685
Lys Ser Ala Glu Pro Ser Val Phe Val Arg Thr Thr Glu Glu Gly Met
        690                 695                 700
Ile Arg Val Arg Lys Ser Lys Gly Lys Tyr Ala Tyr Leu Leu Glu Ser
705                 710                 715                 720
Thr Met Asn Glu Tyr Ile Glu Gln Arg Lys Pro Cys Asp Thr Met Lys
                    725                 730                 735
Val Gly Gly Asn Leu Asp Ser Lys Gly Tyr Gly Ile Ala Thr Pro Lys
                740                 745                 750
Gly Ser Ala Leu Arg Gly Pro Val Asn Leu Ala Val Leu Lys Leu Ser
            755                 760                 765
Glu Gln Gly Val Leu Asp Lys Leu Lys Ser Lys Trp Trp Tyr Asp Lys
        770                 775                 780
Gly Glu Cys Gly Ser Lys Asp Ser Gly Ser Lys Asp Lys Thr Ser Ala
785                 790                 795                 800
Leu Ser Leu Ser Asn Val Ala Gly Val Phe Tyr Ile Leu Ile Gly Gly
                    805                 810                 815
Leu Gly Leu Ala Met Leu Val Ala Leu Ile Glu Phe Cys Tyr Lys Ser
                820                 825                 830
Arg Ser Glu Ser Lys Arg Met Lys Gly Phe Cys Leu Ile Pro Gln Gln
            835                 840                 845
Ser Ile Asn Glu Ala Ile Arg Thr Ser Thr Leu Pro Arg Asn Ser Gly
        850                 855                 860
Ala Gly Ala Ser Gly Ala Gly Ser Gly Glu Asn Gly Arg Val Val Ser
865                 870                 875                 880
His Asp Phe Pro Lys Ser Met Gln Ser Ile Pro Cys Met Ser His Ser
                    885                 890                 895
Ser Gly Met Pro Leu Gly Ala Thr Gly Leu
                900                 905

<210> SEQ ID NO 3
<211> LENGTH: 20
<212> TYPE: DNA
<213> ORGANISM: Artificial
<220> FEATURE:
<223> OTHER INFORMATION: primer GRIA1-F

<400> SEQUENCE: 3
agcctcccta ccagctctct                                              20

<210> SEQ ID NO 4
<211> LENGTH: 18
<212> TYPE: DNA
<213> ORGANISM: Artificial
<220> FEATURE:
<223> OTHER INFORMATION: primer GRIA1-R

<400> SEQUENCE: 4
cgttgttgcc agcctcac                                                18

<210> SEQ ID NO 5
<211> LENGTH: 13161
```

<212> TYPE: DNA
<213> ORGANISM: Bos taurus

<400> SEQUENCE: 5

| | | | | | |
|---|---|---|---|---|---|
| gtgagaggat | gggcagcagg | caagaaagga | ccctgctggt | ctctgcctgc | cctagattcc | 60 |
| tggaacagac | tttctaagag | gagcaagcta | aggaaactag | atccataaag | gctgagggta | 120 |
| tggacactcc | agaatgacaa | tggttttaac | aggatagaca | ttttgctcct | ttttcatata | 180 |
| aacaaaattc | agaagtcagc | aatctggggc | ttgtataatg | gtttcacaat | caccaaaaac | 240 |
| atagcgactt | tttctatctt | cttgttctgc | tatcctcagc | atacagctgc | taccttatag | 300 |
| cccaaaatgg | ctgcagaagc | cccacaatca | cctcagtatt | ctacccatca | ggaagggaaa | 360 |
| aggaaaacag | aaagcaaaac | tgtttcccct | aagaactctt | tccagcagtc | acatacagat | 420 |
| cttctcctca | catgctattg | ccacatctc  | aggaacctac | cccagctagc | tacagcagga | 480 |
| gccagaaaat | ggtgtctcta | ctctgggcag | gatcgccatg | ttgattgagc | ctcctagatt | 540 |
| tgtgcagtgg | gctggtcctt | ctggtcagct | gcatacctgg | ctacaaatca | aggaaattta | 600 |
| actaagcaat | aaccagtaca | tttctgcctc | agagagtcaa | ctcccaatta | tcatgcagac | 660 |
| taccagcctc | tcattccctg | caaggcagct | ttaaactctg | cggctaaaat | ctattttgtt | 720 |
| ttctatttga | aaatggctta | gaataaagat | gagtttctct | gatagctcag | ttggtaaagg | 780 |
| atctgcctgc | aaagcaggag | accccaattc | gattcctggg | tcatgaagat | ccactggaga | 840 |
| agggacagac | tacccactcc | agtattcttg | ggcttccctt | gtggctccgc | tggtaaagag | 900 |
| tcctcctgca | atgcaggaga | cctggattca | atccctgggt | tgggaagatc | tcctggagat | 960 |
| gaagggctac | ccactccagt | attctggcct | agaaaattcc | ttggactgta | tagtacatgg | 1020 |
| ggtcccaaag | aatcagacac | aactgagcga | cattcacttt | cactccagag | taagaataga | 1080 |
| agataatttc | tctttcccac | gtcaaatcta | acagcttggc | agtggctatg | aggaacactg | 1140 |
| ttgagaagga | ttctgagtct | aaatctgttt | atccagggcc | aactgtggat | ccttgccaac | 1200 |
| tttctcttgc | ccctggtcag | ttgcattttg | taaatgtcag | gccactgaac | caagacactg | 1260 |
| tcatcccagt | tttgctcaaa | ctgattcagg | actttagaaa | taaaggcact | tcgacatgac | 1320 |
| cttaagcaaa | caaaatcaca | aatgtgattt | caatcaatga | gtaaactaca | gaggagtttc | 1380 |
| attcattcag | ttcagttcag | ttgctcagtc | gtgtccaact | ccttgtgacc | ccatgagctg | 1440 |
| tagcatgcca | ggcctccctg | tccaacacca | actcccggag | cctacctaaa | ctcacgtcca | 1500 |
| ttgagtcatc | caacccatcc | aaccatctca | ttctctgtcg | tccccttctc | ctcctgccct | 1560 |
| caatctttcc | cagcatcagg | gtcttttcca | atgagtcagc | tcttgcatca | ggtggccaaa | 1620 |
| gtattggagt | tcaggtttta | gcatcattcc | ttccaatgaa | cacccaggcc | ctatctcctt | 1680 |
| tagaatggac | tagttggatc | cccttgcagt | ccaaggaact | ctcaagagtc | ttctccaata | 1740 |
| cacagttcaa | aagcatcaat | tctccggtgc | tcagctttct | ttatagtcca | actctcacat | 1800 |
| ccatacatga | ctactggaaa | aaccatagcc | ttgactagac | gaagttttgt | tggcaaagta | 1860 |
| atgtctctgc | ttttgaatat | gctatctagg | ttggtcataa | cttttccttcc | aaggagtaag | 1920 |
| cgtctttttaa | tttcatggct | gcaatcacca | tctgcagtga | ttttggagcc | cagaaaaata | 1980 |
| aagtctctca | cttttccac | tgtttcctca | tctatttgcc | atgaggtgat | gggaccggat | 2040 |
| gccatgatct | tcgtttctg  | aatgttgagc | tttaagccaa | cttttcact  | ctcctctttc | 2100 |
| actttcatca | agaggctttt | tagtagttct | tcactttctg | ccataagggt | ggtgtcatct | 2160 |
| gcatatctga | ggttattgat | atttctcccg | gcaatcttga | ttctagcttg | tgcttcctcc | 2220 |
| agcccagcgt | ttctcatgat | gtactctgca | tataagttaa | ataagcaggg | tgacaatata | 2280 |

```
cagccttgac gaactccttt tcctatttgg aaccagtctg ttgttccatg tccagttcta   2340
actgatgctt cctgacctgc atacaaattt ctcaagaggc agatcaggtg gtctggtatt   2400
cccacctctt tcaaaatttt ccacagttta ttgtgatcca cacagtcaaa ggctttggca   2460
tagtcaataa agaagaaata gatgttttc tggaactctc ttgctttttt gatgatccag    2520
cggatgttgg caacttgatc tctggttcct ttgtcttttc taaaaccagc ttgaactctg   2580
gaagttcatg gttcatgtat tgctgaagcc tggcttagag aattttgagc attactttac   2640
tagcatgtga gatgagtgca gttgtgtggt agtttgagaa ttctttggca tttcctttct   2700
ttgggattgg aatgaaaact gacctttcc  agtcctgtgg ccactgctga attttccaaa   2760
tttgctggca tattgagtgt agcactttaa cagcatcatc ttttaggatt tgaaatagtt   2820
caactggaat ttgatcacct ccactagctt tgtttgtagt gacgcttcct aaggtccact   2880
tgacttcaca ttccaggatg tctggctcta ggggagtgat cacaccatag taattaactg   2940
ggtcgtgaag atctttttg  tacagttctt ctgtgtattt ttgccaccttt tcttaatat   3000 cttctgcttc tgttaggtcc ataccatttc tgtcctttat tgagcccatc tttgcatgaa   3060
atgttccctt ggtatctcta aatttcttga agagatctct agtctttccc attctatcag   3120
tttcctctat ttctttgcat tgatcgctaa gaagggcttt cttatctctc cttgctattc   3180 tttgaactc  tgcattcaaa taggtgtatc tttccttttcc tcctttccta ttcacttctc   3240
ttcttttcac agctattatt aacatgtgac tatcccactc aatttccaaa agattggaaa   3300
tgattataaa gataccaaat gtaatgtctt tacttaaaa  aggaagtgtt tgtgtgtcca   3360
aactcatgtc cagttcttta caacccccatg aactatagcc tactagactc tttctgacca   3420
tgggatttcc tagacaagaa aacttgagtg gattgccatt tccttctcta gtggatcttc   3480
ccaacgcagg gattgaagcc atgtctcctg cttggcaggt agattgttta ccactgtggc   3540
accagggaag ccccaaaagc aaaaggaaca aaattaaaag ctagaaaaat acctatacat   3600
ttattctaca agactgcact gtgaacttag gatgtaccag agaacatgct agacatcaga   3660
gacaaattga tgagaataga tatgattgct agtgctggaa aatgttgttc tggattgtta   3720
tcttgctttt gtttcaacat tttagtacct tcttagataa gagggggata aaattgaggc   3780
ttagcatgag gaagcacaag aggaaatttt gtggaatata aacttgccac ttgagtgagc   3840
tgcatgcaga aataattaag agcttaccct tctcagatta ttctttttct ttcttttact   3900
gtcaccaggg atggtggagt aaactgttct tcttggctcc cagttggtga cagagagaaa   3960
accaagttgt tttcatggac tgtatcagac agatacagat gagttgtatt taatttagat   4020
gttttgtatt caagctatgc ctcttccccc agatgaacca acattttaac gtggattgga   4080
tagaaaattc tagaattctc tttgaacctc acaaccagca atactactga actcgggagt   4140
tcaggagggc aatattggct agggaggtgg agcagcaggt gcttcgtggc ttacagtggc   4200
tccccgtccc caccataccc cccatccctg gctcactgca ggcatcctca tcaccaggag   4260
gctccttccc agatacagct cccaccagcc tccctaccag ctctctctct gacacccaac   4320
tgtctctgtt cctcccacca gtacacctct gcgctcacct acgatggggt gaaggtgatg   4380
gctgaggctt tccagagcct gcggaggcag agaattgata tctcccgccg ggggaatgct   4440
ggggactgcc tggctaaccc agctgtgccc tggggccagg gcatcgacat ccagagagct   4500
ctgcagcagg tgaggctggc aacaacggtg gccccaccct atgggagcct cgcagggat    4560 ttaagcatca gtgtcaggca ggatatagct attgaaaaaa aaaaaggtgg agcacacccg   4620
aagcttggac caccactgca ttgtttgtgg ctctgacata ggaaaggtca tgtagaaatt   4680
```

```
tgaagaacaa atgaaaaaa cgtaatagta tggaccagtc attcctgaca gcacaagagc    4740
tctattttat gcttagggat tatgctaaga aggggaagcc agtgatgctg tatttgaaag    4800
gggacttgag atacacaagg atgaaactga accattttg caggctctca gagactctgc     4860
tctcttgccc tgattttcta gatttcttta ttatctttgc tctctgtgca catgtcagga    4920
tgggaccctg aaaatgtttc tcgacacttc tgattctatt ttcttgcttc tcagcattgc    4980
actcatcaat tttgtttgca cttacgaatg ggcaaagaac agggatataa aatggtcagg    5040
atcctcctat caactgactc tgcagaggat tctgaggtgg aatccagatt caacagggag    5100
gaatataagc actcagtgat atgtctgctg tggaagcagg atgagacaga tacacgtgag    5160
ccatgtgttt gacattcctg ttttagaagg ttctggggac ttgcccagct ttatgattct    5220
ctgaactcct agaaatctct agaagtttct agaagcacct gaagcacaga ctagttctcc    5280
aagtcctgac ataccaca gtatatgatg cctctgatgc ctcctgagag agaccgtatt      5340
tccaaggggg actgggcaca gagggcaggg ctcacttcac aggaatgtcc aagtatcaga    5400
cacagtggcg agctggcaac agcaaaatgt tctggtgcaa atgactctca ggacatgctc    5460
tctcccagag gggagcattt ctgaatgagg gagaaatgta gaggaaaaca cacaactgtt    5520
accacctgtt ttccagccac acatgcacag ctctagcgat ttacaacctg gagaaacaca    5580
caagatggca atatcatcag ttgttcttta gctcagctga agcacctgca cgtggaggag    5640
aacacagact tctgtccttt ggaatgaagc aaagcaactg ccctgtggct agatgcaaac    5700
ggttccaccc acagcccttt ctgccccacc cccgtcact gtgcagggtg gccccgaatc     5760
cctaggcagc aagagccgga agccagcag cttcagaatg attgccaaag gtgtggtgcc     5820
tgccttctgg cttatttaaa atgctcttcc aggctccaca gtcgacag cttctgtttg      5880 caatgtgaag ctggtttcag aaggtcccag ggacttgccc tcagcttccc agcccttcca    5940
gctcccttgc ctctctcatc ttaaggatgt ccctggaagg atacgctgac atcaccatga    6000
cagtgatgaa gcctggagac aatgtgagtg gcagaaagga ctcttactca ggagacctga    6060
ggtccaagac cagccaggcc cttgagtttc tgggtgacct tgaaatacta attcagatcc    6120
cccacaccct tctctttcct cacccatgac aatgaggcag tcagagagac cactctcagt    6180
tctcacctgg cttacgaatt ctaagcatct aattaatttt ccttacactc taacccatgt    6240 cttctggtt gtaacatgct cagtcttctg tttctgtctt cagtggggtt gagaggaggc     6300
agttgctttc atcaaaataa taatgatctc ctctatacca ggggtcccca aattctagga    6360
tctaatgcct ggtgatctga ggtggagctg gtgtaatatt aataacaata gaaataagta    6420
caaaataaat gtaatgcatt tgaatcatcc tgaagccatg gcaggggcca ctaccctggt    6480
catggaaaaa ttgtcttcca caaaaccggt ccctggtgcc agaaaagatg agaaccatgc    6540
tctataccat cttgaatcaa gacatgcgtg tgccagtcag cttgttcctg cgagcctact    6600
gtatgctctg ccctatgctc tggggacaat tagagaaggc aaggcctgtc tcaagaaac    6660 tctctttagt ctctattgtg gctagaggta gggtgaggag aactagccgc aaaaacagaa    6720
acaaaatata atcaacattc tgatccgaag atcagctgtt caaactgaat caaatatttg    6780
tttatcactt caaatcacaa aaatgtatgg cagaaagaga cctgagaaat gacgactccc    6840
acttttcctt acattagaga tgaagcagct gacccagagt gagcaggaac tcccccagga    6900
tcagcttagc agccgagact gtaacagacc ctgaactggg gctcctcctc ctgcccctag    6960
cctgccctgt ggccccaggg accttggctt gtacgtactg agcctcaggg cctcccacac    7020
acagtcatgg ctgctgtcta gccatttcat cctctagacc catctctta aatagccacg     7080
```

```
ccactaggga gaatctgtgt gcccacagta gacttggtaa atcccaatgc cagtcagtct    7140
ttggacccca acttgggatc tcaaatcact tctaccctga ccttggacct ccaggtcaca    7200
agtcgggagg tatctgaggg ttagcttgtg gtcaagctgg aaagtctgtg agttagacca    7260
ggaggaataa gcacattatt ctaaaactga gggtcatacc agctatgaca tggccagggc    7320
tcactatgca caagcttctg aacatatttt acatgactga tctcactgaa tccctataa    7380
tataaccctc cgaggtagct ggttttatta actgtgcttt ataaatatac acactgagct    7440
acacagatgt tcaagaattc ccccagatta taaactaat tagtggtaaa agtgggattc    7500
caccccacat ctccttgcta cctcactgta cccttaactg ctctgctctg aagcctcgaa    7560
gacccagccc agcagatgag aatgagttct ggcccagcca gctacagcac atggccttgg    7620
gtaatatcca agggcctcag ctcccccctca ccccgctaca gttttcccag gagcagagtg    7680
aagataattc agccgcctgc ctgcccccat ctcctcaccc tgcctgacat ccaaggagcc    7740
actcagaata ttaatgatcc cacaatcctg gaactcctca acgctccagg aaagaggaag    7800
cattagggta cctataagtt ggcttctggc tggcagaaaa gagtgaattc cccaagtcag    7860
gcttttagca tttaggtcat cggcccttttg aggatatgac aggacaaaaa agctttgtac    7920
cttctcccca gaaaaatgca cacacacaca cacacatata tttttgcatg accatgagtc    7980
aggggaaacc acagacactt ccagaagcca agctaagaag ttgaagtgaa gttgaagaac    8040
acctgcccta aataatgatc agccctctta gcgtttgtgt ttgcagtctg tcagccaatg    8100
atcacacaca tcaaagtgaa gattaacagg gcacttcgct agatgaggtc ggggcggggg    8160
gaggggaata agtataagac acagtcctgc aactcaaact gaagacccag tgttgaagga    8220
aagataagct cctaagaaat aatagccata agttgtgga ttcgaagcta aatcacatac    8280
gtagccaggc tgttgatgct ctggatggtc agaaaagaat gctacgactg aggactgtgg    8340
acattaccag actatctgta ggcatgtgtc tggggctta aataggatga ccatataatt    8400
tatcatccaa cctggaacac tggggaatga aagggagagc tatttaccaa ttatcccaga    8460
acaagagatg tagactggat cgatcccagg caaactgaga tggatggtca tgcatgccat    8520
aaaggaagga tgactttaaa caaagagtga tttgggtttt ggagggtctg ggtgaggatg    8580
taaagggtac cagcaggagt ctacagcgag ggtacaagga ggacttcggg ccattgtgct    8640
tggctattag tacgttagga ggacaagagc ggggctctca ccatgcctcc accaagcact    8700
atctggagga tcctggatta attgctcaac ttttctggca ttaatttcct catctcttaa    8760
atgagtataa tcctcataac actgcctccc tttctggctt gtgacaaggc tcaaaatgaa    8820
attttttaaa ggataatata taagtttctt tgatgctcag ggcaactgcc tgagatagct    8880
aaagccagga ttattcttcc cattgatcag gtgggaaagt ggaagctcag aggggtcctg    8940
agacttgctt gccccactag aataaccagc accctggtcc acaggctccg gcttccctag    9000
tgggcattca ggaggagaag ccaagagaac agacctgcct caaggcagcc acaaagaggc    9060
tttagaagcc ccagaccagg gtatctccac tgcccccacc cccagggctg gaggtgcagg    9120
agtcagtcgt cagggctaac ggctcaagta gtaaaaatgc caacaagcac tctcccagca    9180
ccagcaagaa agaacaagta tgcttcagca tctcatggat ggcaaacact gagctggcac    9240
ccaatacaaa tgactggaaa tccaacgtta atcccatc tttcatggag ggagtcagca    9300
ggtgccagga tagtgatagg aggtccaaat ggcaggaact cagggagact ccaggtctcc    9360
cttggcctga ctcctgtcac cccagcgtgg gggtgggagg gaacggggc tcagaggctc    9420
agtactgatg gataggatgg cagtttccag atgtggccaa agcatatgtt tctgagaagc    9480
```

```
ttatttctct aagagtccag actgtcctca taaatggttt ggggctaatc tagtctcctg    9540
acctccccccc ttgctctgcc atcatggaac agtagttctg ggacatattc tttcccacaa    9600
tttaatttat ctcagggtgt gtacatcctg gcttctataa ctagacagta aagagccttc    9660
agctcgccag gcctctcctg acttgctgtg aatcctgaac acaggtgcca cagctctgag    9720
tctcaataat cctacctgta caatcagcaa ataagctct gcttttgcca ctcactgggt    9780
ttctgggaac atcacataag cagcatcctg tgaaatggtg tggcaatgta agaggccctc    9840
aggtcacaga actttgctgc tgctgattat ttttttggga aactgagaaa ggcatgtata    9900
aatgacagcg acaagaccct catttctgct gaaaggatcc cctgctgtga ggtcacaact    9960
tatcacgccc atgttaaatc ttattgtcca tacttcgtac ccactgaaca cagcacagca   10020
gtagtaatag tagtgatcat cattatcttc agcatcacca ccactgaaat cacacacacc   10080
atacattgaa catttatgtc ccagacaata tgctaaacac ttcagtcctt tgaagaggaa   10140
actaggaaac agataggcct agtgacttgt acagaggaat tagagcgtgg cctggggaag   10200
gcccagctag aatagagggt ggcagcggaa tgcctggaga acacacgact ttacacattt   10260
ctgtgtcacc tctcagagcc aaggacagta gcgtgggcct ccatttgaga ggccacttgg   10320
tatatgaagt gacgaaacca gaatatgtca gaagctctgg atttcagacc tgcctcggac   10380
acttgtaagt cctaagtcat gagcaaatca ctttgctatc cagagtctgg gtttctgcca   10440
tgaaagtgat gggacttccc tgatggtcca gtggctggga ctccgtgctc ccagtgcagg   10500
gggcccaggt ttgattcctg gacagggaac tagaccccac atgctgcaac taagacctga   10560
catagccaaa taaataaat aaatattaaa aaaaaaaga aagtgaagat cctaatctct   10620
ctctaaccaa cctatctcag gggttcctct gaatgaagat aaagtaatat gtgccaagtg   10680
tttcataaac acttggaaaa tggtggtaat attaataaca ttattagtaa caataaaaat   10740
aagagttagc ctttgttgaa tacttgccat ggggcaagca ttgatcaaaa aatatctaat   10800
ttcatcctta aaccaacctt aagacataat taaccctaat tggtcctatt aaacaaatga   10860
ggaaactgag tcatagaggc attaggcaat tagcatatga attatgacat aatgataatt   10920
agtatgacac ttgacactgg tgccaaaaat agatgcctct ttgaatcatt aatgacacat   10980
ttctgttcct gcaaatcatc tgcacatctg ttccagtcta ttttttccaaa tgagtcacac   11040
gagctggcac atagcaatga atgggaagct caagatgggc cagagaggac caaggaggga   11100
aggtgaagct gctgatgggt taaaactgct cccgtctcat tccttgtagc aggatcggtg   11160
cttttgctttc cctttgaaaa gcaaaagtag cccagatttt ccagagtgag aatttctcca   11220
gatttcatct cagagagtga agaatgtact gcataatttg ttcagtgctc taggcctgtt   11280
gtgacctccc tactgagact tcaaaccagg aggtgatggg aaggtcagcc tgagaagaga   11340
cacactttc tttcttcctt cctttcttc tttccttcct tccttccctc accctcccac   11400
acaccccatc ttaaatacat acacacaccc cagctattct tgtatcttcc agaggcagag   11460
gggttggtca ttcactgtca gaaaatggtg acacccttca aggcttcctt tgaagcctat   11520
ttgaagaggg gggaaataaa taatgctagg ttagagacat tactttgcca acaaaggtcc   11580
gtctagtcaa ggctatggtt tttcctgtgg tcatgtatgg atgtgagagt tggactgtga   11640
agaattgtga gcgctgaaga attgatgctt ttgaactgtg gtgttggaga agactcttga   11700
gagtcccttg gactgcaagg agatccaacc agtccattct gaaggagatc agccctggga   11760
tttctttgga aggaatgatg ctaaagctga aactccagta ctttggccac ctcatgcgaa   11820
gagttgactc attggaaaag actctgatgc tgggagggat tggggcagg aggaggaggg   11880
```

```
gacgacagag gatgagatgg ctggatggca tcactgactc gatggacatg agtctgagtg   11940
aactccggga gttggtgatg gacagggagg cctggcgtgc tgcgattcat ggggtcgcaa   12000
agagtcggac atgactgagc gactgaactg aattgaactg aactgagagg gcaaggttca   12060
tattggttac aggtacagac ttattggtta caggtacaga ctcatctcac tggccttagg   12120
ccagacaaat ctgaggaaac gtgatagatt atggttggag aatgtgattt ctagtacctg   12180
agctgatgac acgcagctag actcatcccc agtttgaggg tggaccaatt ttattggtca   12240
cctctagagc agcaggcttg gtcccaaaga tcctggatgc tccatgctga ctgctcaccc   12300
tttaaaatga gcctgaagat aggaagccat gaaagtttaa tctgactcat ttgtggagaa   12360
gaaatcctat gaggcatatt tggggcttc ctatatacat gttgattcaa cagctaagac    12420
ctatgtaaag tcctacatga tctggtctta ccataaaggg tttcctcaga tgctttaaag   12480
tttgcataac actttcacat ttgctgtgtc atgtaaggtg gatagagcag gaattttgga   12540
aactagagtc ttggagaggc gatcagccaa tcacttggct gttcagagga aaactggggt   12600
aaaacccagg tcacccaatt ctaggtattc aggttcccag gtattttatt ccctggcctc   12660
acaagggatt acaaagcaac actgaggcat ggcccaaagc atcacaaggc tggctcccag   12720
tcctaggtct tcccctgcct caccagggag ggcacagcag tctcttcctt catgggcctg   12780
cttcagtttc cgcatctgaa ggtgtgtgtc tgaggagcgg tgattctcat ggggtggtcc   12840
tgataggggt atgggactga ggatgacaca aagatttcct atgaagattg acttcgatcc   12900
actcttactg ttggccaaaa gcaatgggtg aagcagtttt caggaagaat ttcattttag   12960
taggagaact gttctccaac agttatgcct gctccaggcc acggagtaga gaggtgttta   13020
ggattgctgc tactctaaga cctcatccca tgtaactttc tcaggttctg ggctttcggt   13080
tcagcaggaa aagccagcaa atgaacaaac atgaagcgca acttcagagt tcactggtca   13140
tcacctggct ttttcttgca g                                            13161
```